United States Patent
Harris et al.

(10) Patent No.: US 9,669,160 B2
(45) Date of Patent: Jun. 6, 2017

(54) TEMPORARY SUSPENSION FOR CLOSED-LOOP MEDICAMENT THERAPY

(71) Applicant: Tandem Diabetes Care, Inc., San Diego, CA (US)

(72) Inventors: Paul Harris, San Diego, CA (US); David Berger, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

(21) Appl. No.: 14/813,699

(22) Filed: Jul. 30, 2015

(65) Prior Publication Data

US 2016/0030669 A1 Feb. 4, 2016

Related U.S. Application Data

(60) Provisional application No. 62/030,933, filed on Jul. 30, 2014.

(51) Int. Cl.
*A61M 5/172* (2006.01)
*A61M 5/142* (2006.01)

(52) U.S. Cl.
CPC ...... *A61M 5/1723* (2013.01); *A61M 5/14244* (2013.01); *A61M 2005/14208* (2013.01); *A61M 2205/502* (2013.01); *A61M 2230/201* (2013.01)

(58) Field of Classification Search
CPC ........ A61M 5/1723; A61M 2005/1726; A61M 5/14244; A61M 2005/14208; A61M 2230/201
See application file for complete search history.

(56) References Cited

U.S. PATENT DOCUMENTS

| | | | |
|---|---|---|---|
| 2,462,596 | A | 2/1949 | Bent |
| 2,629,376 | A | 2/1953 | Pierre et al. |
| 2,691,542 | A | 10/1954 | Chenoweth |
| 3,059,639 | A | 10/1962 | Blackman et al. |
| 4,392,849 | A | 7/1983 | Petre et al. |

(Continued)

FOREIGN PATENT DOCUMENTS

| | | |
|---|---|---|
| DE | 399065 | 7/1924 |
| DE | 4407005 | 3/1995 |

(Continued)

OTHER PUBLICATIONS

PCT Search Report and Written Opinion dated Nov. 11, 2015 for PCT Application No. PCT/US2015/042881, 13 pages.

(Continued)

*Primary Examiner* — Bhisma Mehta
*Assistant Examiner* — Nilay Shah
(74) *Attorney, Agent, or Firm* — Patterson Thuente Pedersen, P.A.

(57) ABSTRACT

A portable infusion pump can communicate with continuous glucose monitor (CGM) to receive continuous feedback relating to a user's blood glucose level during insulin or other medicament therapy and can automatically deliver insulin to a user when the CGM data indicates a need for additional insulin. Because patient behavior can interfere with the accuracy and efficacy of such closed loop or semi-closed loop therapy, a system can employ various mechanisms for manual temporary suspension of closed-loop therapy when a patient is aware that current or future behavior may inhibit therapy.

19 Claims, 5 Drawing Sheets

(56) References Cited

U.S. PATENT DOCUMENTS

| | | |
|---|---|---|
| 4,393,365 A | 7/1983 | Kondo et al. |
| 4,475,901 A | 10/1984 | Kraegen et al. |
| 5,000,664 A | 3/1991 | Lawless et al. |
| 5,050,612 A | 9/1991 | Matsumura |
| 5,122,362 A | 6/1992 | Phillips et al. |
| 5,153,827 A | 10/1992 | Coutre et al. |
| 5,181,910 A | 1/1993 | Scanlon |
| 5,207,666 A | 5/1993 | Idriss et al. |
| 5,219,330 A | 6/1993 | Bollish |
| 5,311,175 A | 5/1994 | Waldman |
| 5,338,157 A | 8/1994 | Blomquist |
| 5,364,346 A | 11/1994 | Schrezenmeir |
| 5,368,562 A | 11/1994 | Blomquist et al. |
| 5,389,078 A | 2/1995 | Zalesky et al. |
| 5,485,408 A | 1/1996 | Blomquist |
| 5,558,638 A | 9/1996 | Evers et al. |
| 5,569,186 A | 10/1996 | Lord et al. |
| 5,658,250 A | 8/1997 | Blomquist et al. |
| 5,658,252 A | 8/1997 | Johnson |
| 5,665,065 A | 9/1997 | Colman et al. |
| 5,669,877 A | 9/1997 | Blomquist |
| 5,681,285 A | 10/1997 | Ford et al. |
| 5,685,844 A | 11/1997 | Marttila |
| 5,695,473 A | 12/1997 | Olsen |
| 5,713,856 A | 2/1998 | Eggers et al. |
| 5,745,378 A | 4/1998 | Barker et al. |
| 5,782,805 A | 7/1998 | Meinzer |
| 5,810,771 A | 9/1998 | Blomquist |
| 5,814,015 A | 9/1998 | Gargano et al. |
| 5,822,715 A | 10/1998 | Worthington et al. |
| 5,876,370 A | 3/1999 | Blomquist |
| 5,879,143 A | 3/1999 | Cote et al. |
| 5,885,211 A | 3/1999 | Eppstein et al. |
| 5,935,099 A | 8/1999 | Peterson et al. |
| 5,935,106 A | 8/1999 | Olsen |
| 6,023,629 A | 2/2000 | Tamada |
| 6,024,539 A | 2/2000 | Blomquist |
| 6,077,055 A | 6/2000 | Vilks |
| 6,122,536 A | 9/2000 | Sun et al. |
| 6,142,939 A | 11/2000 | Eppstein et al. |
| 6,233,471 B1 | 5/2001 | Berner et al. |
| 6,241,704 B1 | 6/2001 | Peterson et al. |
| 6,248,057 B1 | 6/2001 | Mavity et al. |
| 6,248,067 B1 | 6/2001 | Causey, III et al. |
| 6,249,717 B1 | 6/2001 | Nicholson et al. |
| 6,272,364 B1 | 8/2001 | Kurnik |
| 6,298,254 B2 | 10/2001 | Tamada |
| 6,306,420 B1 | 10/2001 | Cheikh |
| 6,368,272 B1 | 4/2002 | Porumbescu |
| 6,379,301 B1 | 4/2002 | Worthington et al. |
| 6,422,057 B1 | 7/2002 | Anderson |
| 6,475,180 B2 | 11/2002 | Peterson et al. |
| 6,505,059 B1 | 1/2003 | Kollias et al. |
| 6,517,482 B1 | 2/2003 | Elden et al. |
| 6,539,250 B1 | 3/2003 | Bettinger |
| 6,544,212 B2 | 4/2003 | Galley et al. |
| 6,546,269 B1 | 4/2003 | Kurnik |
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,571,128 B2 | 5/2003 | Lebel et al. |
| 6,577,899 B2 | 6/2003 | Lebel et al. |
| 6,582,366 B1 | 6/2003 | Porumbescu |
| 6,595,919 B2 | 7/2003 | Berner et al. |
| 6,623,698 B2 | 9/2003 | Kuo |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,114 B1 | 12/2003 | Poulsen et al. |
| 6,659,978 B1 | 12/2003 | Kasuga et al. |
| 6,668,196 B1 | 12/2003 | Villegas et al. |
| 6,687,522 B2 | 2/2004 | Tamada |
| 6,694,191 B2 | 2/2004 | Starkweather et al. |
| 6,740,072 B2 | 5/2004 | Starkweather et al. |
| 6,740,075 B2 | 5/2004 | Lebel et al. |
| 6,744,350 B2 | 6/2004 | Blomquist |
| 6,771,250 B1 | 8/2004 | Oh |
| 6,773,412 B2 | 8/2004 | O'Mahony |
| 6,790,198 B1 | 9/2004 | White et al. |
| 6,809,653 B1 | 10/2004 | Mann et al. |
| 6,810,290 B2 | 10/2004 | Lebel et al. |
| 6,835,175 B1 | 12/2004 | Porumbescu |
| 6,852,104 B2 | 2/2005 | Blomquist |
| 6,872,200 B2 | 3/2005 | Mann et al. |
| 6,873,268 B2 | 3/2005 | Lebel et al. |
| 6,880,564 B2 | 4/2005 | Erickson |
| 6,882,940 B2 | 4/2005 | Potts et al. |
| 6,895,263 B2 | 5/2005 | Shin et al. |
| 6,902,905 B2 | 6/2005 | Burson et al. |
| 6,934,220 B1 | 8/2005 | Cruitt et al. |
| 6,936,029 B2 | 8/2005 | Mann et al. |
| 6,957,655 B2 | 10/2005 | Erickson et al. |
| 6,958,705 B2 | 10/2005 | Lebel et al. |
| 6,966,325 B2 | 11/2005 | Erickson |
| 6,970,742 B2 | 11/2005 | Mann et al. |
| 6,974,437 B2 | 12/2005 | Lebel et al. |
| 6,979,326 B2 | 12/2005 | Mann et al. |
| 6,997,920 B2 | 2/2006 | Mann et al. |
| 6,998,387 B1 | 2/2006 | Goke et al. |
| 6,999,854 B2 | 2/2006 | Roth |
| 7,004,928 B2 | 2/2006 | Aceti et al. |
| 7,025,743 B2 | 4/2006 | Mann et al. |
| 7,033,338 B2 | 4/2006 | Vilks et al. |
| 7,041,082 B2 | 5/2006 | Blomquist et al. |
| 7,098,803 B2 | 8/2006 | Mann et al. |
| 7,109,878 B2 | 9/2006 | Mann et al. |
| 7,150,741 B2 | 12/2006 | Erickson et al. |
| 7,179,226 B2 | 2/2007 | Crothall et al. |
| 7,181,505 B2 | 2/2007 | Haller et al. |
| 7,183,068 B2 | 2/2007 | Burson et al. |
| 7,204,823 B2 | 4/2007 | Estes et al. |
| 7,231,263 B2 | 6/2007 | Choi |
| 7,247,702 B2 | 7/2007 | Gardner et al. |
| 7,267,665 B2 | 9/2007 | Steil et al. |
| 7,278,983 B2 | 10/2007 | Ireland et al. |
| 7,282,029 B1 | 10/2007 | Poulsen et al. |
| 7,291,107 B2 | 11/2007 | Hellwig et al. |
| 7,295,867 B2 | 11/2007 | Berner et al. |
| 7,307,245 B2 | 12/2007 | Faries, Jr. et al. |
| 7,324,012 B2 | 1/2008 | Mann et al. |
| 7,341,577 B2 | 3/2008 | Gill |
| 7,399,277 B2 | 7/2008 | Saidara et al. |
| 7,404,796 B2 | 7/2008 | Ginsberg |
| 7,446,091 B2 | 11/2008 | Van Den Berghe |
| 7,471,994 B2 | 12/2008 | Ford et al. |
| 7,483,743 B2 | 1/2009 | Mann et al. |
| 7,491,187 B2 | 2/2009 | Van Den Berghe |
| 7,497,827 B2 | 3/2009 | Brister et al. |
| 7,515,060 B2 | 4/2009 | Blomquist |
| 7,553,281 B2 | 6/2009 | Hellwig et al. |
| 7,556,613 B2 | 7/2009 | Wittmann et al. |
| 7,559,926 B1 | 7/2009 | Blischak |
| 7,588,046 B1 | 9/2009 | Erickson |
| 7,591,801 B2 | 9/2009 | Brauker et al. |
| 7,647,237 B2 | 1/2010 | Malave et al. |
| 7,651,489 B2 | 1/2010 | Estes et al. |
| 7,651,845 B2 | 1/2010 | Doyle et al. |
| 7,674,485 B2 | 3/2010 | Bhaskaran et al. |
| 7,678,071 B2 | 3/2010 | Lebel et al. |
| 7,678,762 B2 | 3/2010 | Green et al. |
| 7,678,763 B2 | 3/2010 | Green et al. |
| 7,687,272 B1 | 3/2010 | Buchwald et al. |
| 7,704,226 B2 | 4/2010 | Mueller et al. |
| 7,711,402 B2 | 5/2010 | Shults et al. |
| 7,715,893 B2 | 5/2010 | Kamath et al. |
| 7,717,903 B2 | 5/2010 | Estes et al. |
| 7,734,323 B2 | 6/2010 | Blomquist et al. |
| 7,751,907 B2 | 7/2010 | Blomquist |
| 7,766,829 B2 | 8/2010 | Sloan et al. |
| 7,768,386 B2 | 8/2010 | Hayter et al. |
| 7,768,408 B2 | 8/2010 | Reggiardo et al. |

(56) References Cited

U.S. PATENT DOCUMENTS

| | | |
|---|---|---|
| 7,774,145 B2 | 8/2010 | Brauker et al. |
| 7,785,313 B2 | 8/2010 | Mastrototaro |
| 7,806,853 B2 | 10/2010 | Wittmann et al. |
| 7,806,886 B2 | 10/2010 | Kanderian, Jr. et al. |
| 7,815,602 B2 | 10/2010 | Mann et al. |
| 7,819,843 B2 | 10/2010 | Mann et al. |
| 7,837,647 B2 | 11/2010 | Estes et al. |
| 7,869,851 B2 | 1/2011 | Hellwig et al. |
| 7,875,022 B2 | 1/2011 | Wenger et al. |
| 7,884,729 B2 | 2/2011 | Reggiardo et al. |
| 7,890,295 B2 | 2/2011 | Shin et al. |
| 7,912,674 B2 | 3/2011 | Killoren et al. |
| 7,914,499 B2 | 3/2011 | Gonnelli et al. |
| 7,920,907 B2 | 4/2011 | McGarraugh et al. |
| 7,935,076 B2 | 5/2011 | Estes et al. |
| 7,941,200 B2 | 5/2011 | Weinert et al. |
| 7,946,985 B2 | 5/2011 | Mastrototaro et al. |
| 7,959,598 B2 | 6/2011 | Estes |
| 7,967,773 B2 | 6/2011 | Amborn et al. |
| 7,972,296 B2 | 7/2011 | Braig et al. |
| 7,976,492 B2 | 7/2011 | Brauker et al. |
| 7,981,034 B2 | 7/2011 | Jennewine et al. |
| 7,985,330 B2 | 7/2011 | Wang et al. |
| 7,996,158 B2 | 8/2011 | Hayter et al. |
| 8,005,524 B2 | 8/2011 | Brauker et al. |
| 8,012,119 B2 | 9/2011 | Estes et al. |
| 8,029,459 B2 | 10/2011 | Rush et al. |
| 8,029,460 B2 | 10/2011 | Rush et al. |
| 8,062,249 B2 | 11/2011 | Wilinska et al. |
| 8,066,665 B2 | 11/2011 | Rush et al. |
| 8,075,527 B2 | 12/2011 | Rush et al. |
| 8,079,983 B2 | 12/2011 | Rush et al. |
| 8,079,984 B2 | 12/2011 | Rush et al. |
| 8,083,718 B2 | 12/2011 | Rush et al. |
| 8,088,098 B2 | 1/2012 | Yodfat et al. |
| 8,093,212 B2 | 1/2012 | Gardner et al. |
| 8,109,921 B2 | 2/2012 | Estes et al. |
| 8,114,350 B1 | 2/2012 | Silver et al. |
| 8,119,593 B2 | 2/2012 | Richardson et al. |
| 8,127,046 B2 | 2/2012 | Grant et al. |
| 8,129,429 B2 | 3/2012 | Sporn et al. |
| 8,140,312 B2 | 3/2012 | Hayter et al. |
| 8,147,446 B2 | 4/2012 | Yodfat et al. |
| 8,152,789 B2 | 4/2012 | Starkweather et al. |
| 8,170,721 B2 | 5/2012 | Nickerson |
| 8,192,394 B2 | 6/2012 | Estes et al. |
| 8,192,395 B2 | 6/2012 | Estes et al. |
| 8,202,267 B2 | 6/2012 | Field et al. |
| 8,204,729 B2 | 6/2012 | Sher |
| 8,206,296 B2 | 6/2012 | Jennewine |
| 8,206,350 B2 | 6/2012 | Mann et al. |
| 8,208,984 B2 | 6/2012 | Blomquist et al. |
| 8,219,222 B2 | 7/2012 | Blomquist |
| 8,221,345 B2 | 7/2012 | Blomquist |
| 8,226,891 B2 | 7/2012 | Sloan et al. |
| 8,231,562 B2 | 7/2012 | Buck et al. |
| 8,234,126 B1 | 7/2012 | Estes |
| 8,234,128 B2 | 7/2012 | Martucci et al. |
| 8,237,715 B2 | 8/2012 | Buck et al. |
| 8,246,540 B2 | 8/2012 | Ginsberg |
| 8,250,483 B2 | 8/2012 | Blomquist |
| 8,251,904 B2 | 8/2012 | Zivitz et al. |
| 8,251,906 B2 | 8/2012 | Brauker et al. |
| 8,257,259 B2 | 9/2012 | Brauker et al. |
| 8,257,300 B2 | 9/2012 | Budiman et al. |
| 8,262,617 B2 | 9/2012 | Aeschlimann et al. |
| 8,287,454 B2 | 10/2012 | Wolpert et al. |
| 8,287,495 B2 | 10/2012 | Michaud et al. |
| 8,287,514 B2 | 10/2012 | Miller et al. |
| 8,311,749 B2 | 11/2012 | Brauker et al. |
| 8,328,754 B2 | 12/2012 | Estes et al. |
| 8,343,092 B2 | 1/2013 | Rush et al. |
| 8,344,847 B2 | 1/2013 | Moberg et al. |
| 8,346,399 B2 | 1/2013 | Blomquist |
| 8,348,885 B2 | 1/2013 | Moberg et al. |
| 8,348,886 B2 | 1/2013 | Kanderian, Jr. et al. |
| 8,348,923 B2 | 1/2013 | Kanderian, Jr. et al. |
| 8,372,040 B2 | 2/2013 | Huang et al. |
| 8,414,523 B2 | 4/2013 | Blomquist et al. |
| 8,451,230 B2 | 5/2013 | Celentano et al. |
| 8,452,953 B2 | 5/2013 | Buck et al. |
| 8,454,510 B2 | 6/2013 | Yodfat et al. |
| 8,454,576 B2 | 6/2013 | Mastrototaro |
| 8,454,581 B2 | 6/2013 | Estes et al. |
| 8,460,231 B2 | 6/2013 | Brauker et al. |
| 8,465,460 B2 | 6/2013 | Yodfat et al. |
| 8,552,880 B2 | 10/2013 | Kopp et al. |
| 8,562,558 B2 | 10/2013 | Kamath et al. |
| 8,573,027 B2 | 11/2013 | Rosinko et al. |
| 8,579,853 B2 | 11/2013 | Reggiardo et al. |
| 8,650,937 B2 | 2/2014 | Brown |
| 8,657,779 B2 | 2/2014 | Blomquist |
| 8,712,748 B2 | 4/2014 | Thukral et al. |
| 8,718,949 B2 | 5/2014 | Blomquist et al. |
| 8,801,657 B2 | 8/2014 | Blomquist et al. |
| 8,882,701 B2 | 11/2014 | DeBelser et al. |
| 8,986,253 B2 | 3/2015 | DiPerna |
| 9,008,803 B2 | 4/2015 | Blomquist |
| 2001/0001144 A1 | 5/2001 | Kapp |
| 2001/0031944 A1 | 10/2001 | Peterson et al. |
| 2001/0037217 A1 | 11/2001 | Abensour et al. |
| 2001/0041831 A1 | 11/2001 | Starkweather |
| 2002/0002326 A1 | 1/2002 | Causey, III et al. |
| 2002/0065454 A1 | 5/2002 | Lebel et al. |
| 2002/0072932 A1 | 6/2002 | Swamy |
| 2002/0077852 A1 | 6/2002 | Ford et al. |
| 2002/0107476 A1 | 8/2002 | Mann et al. |
| 2002/0143580 A1 | 10/2002 | Bristol et al. |
| 2002/0183693 A1 | 12/2002 | Peterson et al. |
| 2002/0193679 A1 | 12/2002 | Malave et al. |
| 2003/0032867 A1 | 2/2003 | Crothall et al. |
| 2003/0036683 A1 | 2/2003 | Kehr et al. |
| 2003/0050621 A1 | 3/2003 | Lebel et al. |
| 2003/0060765 A1* | 3/2003 | Campbell .......... A61M 5/14244 604/131 |
| 2003/0065308 A1 | 4/2003 | Lebel et al. |
| 2003/0088238 A1 | 5/2003 | Poulsen et al. |
| 2003/0114836 A1 | 6/2003 | Estes et al. |
| 2003/0130616 A1 | 7/2003 | Steil et al. |
| 2003/0160683 A1 | 8/2003 | Blomquist |
| 2003/0161744 A1 | 8/2003 | Vilks et al. |
| 2003/0163088 A1 | 8/2003 | Blomquist |
| 2003/0163090 A1 | 8/2003 | Blomquist et al. |
| 2003/0163223 A1 | 8/2003 | Blomquist |
| 2003/0163789 A1 | 8/2003 | Blomquist |
| 2003/0199854 A1 | 10/2003 | Kovach et al. |
| 2003/0208113 A1 | 11/2003 | Mault et al. |
| 2003/0212364 A1 | 11/2003 | Mann et al. |
| 2003/0212379 A1 | 11/2003 | Bylund et al. |
| 2003/0236489 A1 | 12/2003 | Jacobson et al. |
| 2004/0015102 A1 | 1/2004 | Cummings et al. |
| 2004/0015132 A1 | 1/2004 | Brown |
| 2004/0068230 A1 | 4/2004 | Estes et al. |
| 2004/0073095 A1 | 4/2004 | Causey, III et al. |
| 2004/0115067 A1 | 6/2004 | Rush et al. |
| 2004/0152622 A1 | 8/2004 | Keith |
| 2004/0180810 A1 | 9/2004 | Pilarski |
| 2004/0193025 A1 | 9/2004 | Steil et al. |
| 2004/0193090 A1 | 9/2004 | Lebel et al. |
| 2004/0225252 A1 | 11/2004 | Gillespie, Jr. et al. |
| 2004/0254434 A1 | 12/2004 | Goodnow et al. |
| 2005/0021006 A1 | 1/2005 | Tonnies |
| 2005/0022274 A1 | 1/2005 | Campbell et al. |
| 2005/0030164 A1 | 2/2005 | Blomquist |
| 2005/0065760 A1 | 3/2005 | Murtfeldt et al. |
| 2005/0095063 A1 | 5/2005 | Fathallah et al. |
| 2005/0137530 A1 | 6/2005 | Campbell et al. |
| 2005/0143864 A1 | 6/2005 | Blomquist |
| 2005/0171513 A1 | 8/2005 | Mann et al. |
| 2005/0197553 A1 | 9/2005 | Cooper |
| 2005/0197621 A1 | 9/2005 | Poulsen et al. |
| 2005/0203349 A1 | 9/2005 | Nanikashvili |
| 2005/0203360 A1 | 9/2005 | Brauker et al. |
| 2005/0272640 A1 | 12/2005 | Doyle et al. |

(56) References Cited

U.S. PATENT DOCUMENTS

| | | |
|---|---|---|
| 2005/0277872 A1 | 12/2005 | Colby et al. |
| 2006/0001550 A1 | 1/2006 | Mann et al. |
| 2006/0014670 A1 | 1/2006 | Green et al. |
| 2006/0047192 A1 | 3/2006 | Hellwig et al. |
| 2006/0047538 A1 | 3/2006 | Condurso et al. |
| 2006/0080059 A1 | 4/2006 | Stupp et al. |
| 2006/0085223 A1 | 4/2006 | Anderson et al. |
| 2006/0094985 A1 | 5/2006 | Aceti et al. |
| 2006/0122577 A1 | 6/2006 | Poulsen et al. |
| 2006/0132292 A1 | 6/2006 | Blomquist |
| 2006/0137695 A1 | 6/2006 | Hellwig et al. |
| 2006/0167345 A1 | 7/2006 | Vespasiani |
| 2006/0173406 A1 | 8/2006 | Hayes et al. |
| 2006/0173444 A1 | 8/2006 | Choy et al. |
| 2006/0202859 A1 | 9/2006 | Mastrototaro et al. |
| 2006/0224109 A1 | 10/2006 | Steil et al. |
| 2006/0253097 A1 | 11/2006 | Braig et al. |
| 2006/0264895 A1 | 11/2006 | Flanders |
| 2006/0271020 A1 | 11/2006 | Huang et al. |
| 2006/0276771 A1 | 12/2006 | Galley et al. |
| 2007/0016127 A1 | 1/2007 | Staib et al. |
| 2007/0021733 A1 | 1/2007 | Hansen et al. |
| 2007/0033074 A1 | 2/2007 | Nitzan et al. |
| 2007/0060796 A1 | 3/2007 | Kim |
| 2007/0060871 A1 | 3/2007 | Istoc et al. |
| 2007/0060874 A1 | 3/2007 | Nesbitt et al. |
| 2007/0066956 A1* | 3/2007 | Finkel .............. A61M 5/142 604/500 |
| 2007/0083152 A1 | 4/2007 | Williams, Jr. |
| 2007/0093786 A1 | 4/2007 | Goldsmith et al. |
| 2007/0100222 A1 | 5/2007 | Mastrototaro et al. |
| 2007/0106135 A1 | 5/2007 | Sloan et al. |
| 2007/0112298 A1 | 5/2007 | Mueller, Jr. |
| 2007/0112299 A1 | 5/2007 | Smit et al. |
| 2007/0118405 A1 | 5/2007 | Campbell et al. |
| 2007/0124002 A1 | 5/2007 | Estes et al. |
| 2007/0149861 A1 | 6/2007 | Crothall et al. |
| 2007/0156033 A1 | 7/2007 | Causey, III et al. |
| 2007/0173712 A1 | 7/2007 | Shah et al. |
| 2007/0203454 A1 | 8/2007 | Shermer et al. |
| 2007/0213657 A1 | 9/2007 | Jennewine et al. |
| 2007/0233051 A1 | 10/2007 | Hohl et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255250 A1 | 11/2007 | Moberg et al. |
| 2007/0258395 A1 | 11/2007 | Jollota et al. |
| 2007/0287985 A1 | 12/2007 | Estes et al. |
| 2007/0299389 A1 | 12/2007 | Halbert et al. |
| 2008/0004601 A1 | 1/2008 | Jennewine et al. |
| 2008/0030369 A1 | 2/2008 | Mann et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0051709 A1 | 2/2008 | Mounce et al. |
| 2008/0051714 A1 | 2/2008 | Moberg et al. |
| 2008/0051716 A1 | 2/2008 | Stutz |
| 2008/0058773 A1 | 3/2008 | John |
| 2008/0065007 A1 | 3/2008 | Peterson |
| 2008/0065016 A1 | 3/2008 | Peterson |
| 2008/0071209 A1 | 3/2008 | Moubayed |
| 2008/0071210 A1 | 3/2008 | Moubayed |
| 2008/0071217 A1 | 3/2008 | Moubayed |
| 2008/0071251 A1 | 3/2008 | Moubayed et al. |
| 2008/0076969 A1 | 3/2008 | Kraft et al. |
| 2008/0097289 A1 | 4/2008 | Steil et al. |
| 2008/0106431 A1 | 5/2008 | Blomquist |
| 2008/0114299 A1 | 5/2008 | Damgaard-Sorensen et al. |
| 2008/0132844 A1 | 6/2008 | Peterson |
| 2008/0139907 A1 | 6/2008 | Rao et al. |
| 2008/0147004 A1 | 6/2008 | Mann et al. |
| 2008/0147041 A1 | 6/2008 | Kristensen et al. |
| 2008/0147050 A1 | 6/2008 | Mann et al. |
| 2008/0154513 A1 | 6/2008 | Kovatchev et al. |
| 2008/0171697 A1 | 7/2008 | Jacotot et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0177165 A1 | 7/2008 | Blomquist et al. |
| 2008/0183060 A1 | 7/2008 | Steil et al. |
| 2008/0206799 A1 | 8/2008 | Blomquist |
| 2008/0228056 A1 | 9/2008 | Blomquist et al. |
| 2008/0249470 A1 | 10/2008 | Malave et al. |
| 2008/0255517 A1 | 10/2008 | Nair et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287922 A1 | 11/2008 | Panduro |
| 2008/0288115 A1 | 11/2008 | Rusnak et al. |
| 2008/0294024 A1 | 11/2008 | Cosentino et al. |
| 2008/0294142 A1 | 11/2008 | Patel et al. |
| 2008/0294294 A1 | 11/2008 | Blomquist |
| 2008/0300534 A1 | 12/2008 | Blomquist |
| 2008/0300572 A1 | 12/2008 | Rankers |
| 2008/0306434 A1 | 12/2008 | Dobbles et al. |
| 2008/0306444 A1 | 12/2008 | Brister et al. |
| 2008/0312585 A1 | 12/2008 | Brukalo et al. |
| 2009/0005726 A1 | 1/2009 | Jones et al. |
| 2009/0036753 A1 | 2/2009 | King |
| 2009/0069745 A1 | 3/2009 | Estes et al. |
| 2009/0069749 A1 | 3/2009 | Miller et al. |
| 2009/0069787 A1 | 3/2009 | Estes et al. |
| 2009/0088731 A1 | 4/2009 | Campbell et al. |
| 2009/0093756 A1 | 4/2009 | Minaie |
| 2009/0105636 A1* | 4/2009 | Hayter ................ A61M 5/1723 604/66 |
| 2009/0105646 A1 | 4/2009 | Hendrixson et al. |
| 2009/0131860 A1 | 5/2009 | Nielsen |
| 2009/0131861 A1 | 5/2009 | Braig et al. |
| 2009/0156990 A1 | 6/2009 | Wenger et al. |
| 2009/0163855 A1 | 6/2009 | Shin et al. |
| 2009/0171269 A1 | 7/2009 | Jennewine et al. |
| 2009/0177142 A1 | 7/2009 | Blomquist et al. |
| 2009/0177147 A1 | 7/2009 | Blomquist et al. |
| 2009/0177154 A1 | 7/2009 | Blomquist et al. |
| 2009/0177180 A1 | 7/2009 | Rubalcaba |
| 2009/0192366 A1 | 7/2009 | Mensinger et al. |
| 2009/0192724 A1 | 7/2009 | Bauker et al. |
| 2009/0192745 A1 | 7/2009 | Kamath et al. |
| 2009/0212966 A1 | 8/2009 | Panduro |
| 2009/0247931 A1 | 10/2009 | Damgaard-Sorensen |
| 2009/0247982 A1 | 10/2009 | Krulevitch et al. |
| 2009/0254037 A1 | 10/2009 | Bryant, Jr. et al. |
| 2009/0267774 A1 | 10/2009 | Enegren et al. |
| 2009/0267775 A1 | 10/2009 | Enegren et al. |
| 2009/0270705 A1 | 10/2009 | Enegren et al. |
| 2009/0281393 A1 | 11/2009 | Smith |
| 2010/0008795 A1 | 1/2010 | DiPerna |
| 2010/0010330 A1 | 1/2010 | Rankers et al. |
| 2010/0030045 A1 | 2/2010 | Gottlieb et al. |
| 2010/0030387 A1 | 2/2010 | Sen |
| 2010/0056993 A1 | 3/2010 | Chase |
| 2010/0057043 A1 | 3/2010 | Kovatchev et al. |
| 2010/0064257 A1 | 3/2010 | Buck et al. |
| 2010/0081993 A1 | 4/2010 | O'Connor |
| 2010/0095229 A1 | 4/2010 | Dixon et al. |
| 2010/0105999 A1 | 4/2010 | Dixon et al. |
| 2010/0114015 A1 | 5/2010 | Kanderian, Jr. et al. |
| 2010/0121169 A1 | 5/2010 | Petisce et al. |
| 2010/0121170 A1 | 5/2010 | Rule |
| 2010/0125241 A1 | 5/2010 | Prud et al. |
| 2010/0130933 A1 | 5/2010 | Holland et al. |
| 2010/0138197 A1 | 6/2010 | Sher |
| 2010/0145276 A1 | 6/2010 | Yodfat et al. |
| 2010/0160740 A1 | 6/2010 | Cohen et al. |
| 2010/0161236 A1 | 6/2010 | Cohen et al. |

(56) References Cited

U.S. PATENT DOCUMENTS

| | | |
|---|---|---|
| 2010/0161346 A1 | 6/2010 | Getschmann et al. |
| 2010/0162786 A1 | 7/2010 | Keenan et al. |
| 2010/0174266 A1 | 7/2010 | Estes |
| 2010/0174553 A1 | 7/2010 | Kaufman et al. |
| 2010/0179402 A1 | 7/2010 | Goode et al. |
| 2010/0185142 A1 | 7/2010 | Kamen et al. |
| 2010/0185175 A1 | 7/2010 | Kamen et al. |
| 2010/0198142 A1 | 8/2010 | Sloan et al. |
| 2010/0218132 A1 | 8/2010 | Soni et al. |
| 2010/0222765 A1 | 9/2010 | Blomquist et al. |
| 2010/0228186 A1 | 9/2010 | Estes et al. |
| 2010/0261987 A1 | 10/2010 | Kamath et al. |
| 2010/0262117 A1 | 10/2010 | Magni et al. |
| 2010/0262434 A1 | 10/2010 | Shaya |
| 2010/0274751 A1 | 10/2010 | Blomquist |
| 2010/0286601 A1 | 11/2010 | Yodfat et al. |
| 2010/0286653 A1 | 11/2010 | Kubel et al. |
| 2010/0292634 A1 | 11/2010 | Kircher et al. |
| 2010/0295686 A1 | 11/2010 | Sloan et al. |
| 2010/0298685 A1 | 11/2010 | Hayter et al. |
| 2010/0305545 A1 | 12/2010 | Kanderian, Jr. et al. |
| 2010/0312085 A1 | 12/2010 | Andrews et al. |
| 2010/0324382 A1 | 12/2010 | Cantwell et al. |
| 2010/0324398 A1 | 12/2010 | Tzyy-Ping |
| 2010/0331651 A1 | 12/2010 | Groll |
| 2011/0004188 A1 | 1/2011 | Shekalim |
| 2011/0033833 A1 | 2/2011 | Blomquist et al. |
| 2011/0040247 A1 | 2/2011 | Mandro et al. |
| 2011/0040251 A1 | 2/2011 | Blomquist |
| 2011/0047499 A1 | 2/2011 | Mandro et al. |
| 2011/0053121 A1 | 3/2011 | Heaton |
| 2011/0054390 A1 | 3/2011 | Searle et al. |
| 2011/0054391 A1 | 3/2011 | Ward et al. |
| 2011/0056264 A1 | 3/2011 | Kaplan |
| 2011/0058485 A1 | 3/2011 | Sloan |
| 2011/0060281 A1 | 3/2011 | Aeschlimann et al. |
| 2011/0071372 A1 | 3/2011 | Sloan et al. |
| 2011/0071765 A1 | 3/2011 | Yodfat et al. |
| 2011/0082439 A1 | 4/2011 | Wenger et al. |
| 2011/0087165 A1 | 4/2011 | Amborn et al. |
| 2011/0092788 A1 | 4/2011 | Long et al. |
| 2011/0098548 A1 | 4/2011 | Budiman et al. |
| 2011/0098637 A1 | 4/2011 | Hill |
| 2011/0098638 A1 | 4/2011 | Chawla et al. |
| 2011/0098674 A1 | 4/2011 | Vicente et al. |
| 2011/0106011 A1 | 5/2011 | Cinar et al. |
| 2011/0106050 A1 | 5/2011 | Yodfat et al. |
| 2011/0112505 A1 | 5/2011 | Starkweather et al. |
| 2011/0112506 A1 | 5/2011 | Starkweather et al. |
| 2011/0118578 A1 | 5/2011 | Timmerman |
| 2011/0118699 A1 | 5/2011 | Yodfat et al. |
| 2011/0124996 A1 | 5/2011 | Reinke et al. |
| 2011/0124999 A1 | 5/2011 | Reggiardo et al. |
| 2011/0126188 A1 | 5/2011 | Bernstein et al. |
| 2011/0130746 A1 | 6/2011 | Budiman |
| 2011/0137239 A1 | 6/2011 | DeBelser |
| 2011/0144586 A1 | 6/2011 | Michaud et al. |
| 2011/0152770 A1 | 6/2011 | DiPerna et al. |
| 2011/0160654 A1 | 6/2011 | Hanson et al. |
| 2011/0166544 A1 | 7/2011 | Verhoef et al. |
| 2011/0166875 A1 | 7/2011 | Hayter et al. |
| 2011/0178461 A1 | 7/2011 | Chong et al. |
| 2011/0178717 A1 | 7/2011 | Goodnow et al. |
| 2011/0184342 A1* | 7/2011 | Pesach .............. A61M 5/14248 604/65 |
| 2011/0190701 A1 | 8/2011 | Remde et al. |
| 2011/0196213 A1 | 8/2011 | Thukral et al. |
| 2011/0202040 A1 | 8/2011 | Remde et al. |
| 2011/0205065 A1 | 8/2011 | Strachan et al. |
| 2011/0208155 A1 | 8/2011 | Palerm et al. |
| 2011/0213306 A1 | 9/2011 | Hanson et al. |
| 2011/0257625 A1 | 10/2011 | Jasperson et al. |
| 2011/0257895 A1 | 10/2011 | Brauker et al. |
| 2011/0266999 A1 | 11/2011 | Yodfat et al. |
| 2012/0029941 A1 | 2/2012 | Malave et al. |
| 2012/0030610 A1 | 2/2012 | DiPerna et al. |
| 2012/0041415 A1 | 2/2012 | Estes et al. |
| 2012/0053522 A1 | 3/2012 | Yodfat et al. |
| 2012/0059353 A1 | 3/2012 | Kovatchev et al. |
| 2012/0095315 A1 | 4/2012 | Tenbarge et al. |
| 2012/0109100 A1 | 5/2012 | Estes et al. |
| 2012/0123230 A1 | 5/2012 | Brown et al. |
| 2012/0191061 A1 | 7/2012 | Yodfat et al. |
| 2012/0191063 A1 | 7/2012 | Brauker et al. |
| 2012/0226124 A1 | 9/2012 | Blomquist |
| 2012/0232484 A1 | 9/2012 | Blomquist |
| 2012/0232485 A1 | 9/2012 | Blomquist |
| 2012/0232520 A1 | 9/2012 | Sloan et al. |
| 2012/0232521 A1 | 9/2012 | Blomquist |
| 2012/0238852 A1 | 9/2012 | Brauker et al. |
| 2012/0238854 A1 | 9/2012 | Blomquist et al. |
| 2012/0239362 A1 | 9/2012 | Blomquist |
| 2012/0245524 A1 | 9/2012 | Estes et al. |
| 2012/0265722 A1 | 10/2012 | Blomquist |
| 2012/0296269 A1 | 11/2012 | Blomquist |
| 2012/0330227 A1 | 12/2012 | Budiman et al. |
| 2013/0053816 A1 | 2/2013 | DiPerna et al. |
| 2013/0131630 A1 | 5/2013 | Blomquist |
| 2013/0324928 A1 | 12/2013 | Kruse |
| 2013/0331790 A1 | 12/2013 | Brown et al. |
| 2013/0345625 A1 | 12/2013 | Causey, III |
| 2014/0012511 A1 | 1/2014 | Mensinger et al. |
| 2014/0019396 A1 | 1/2014 | Carlsgaard et al. |
| 2014/0066890 A1 | 3/2014 | Sloan et al. |
| 2014/0074059 A1 | 3/2014 | Howell et al. |
| 2014/0137641 A1 | 5/2014 | Brown |
| 2014/0171772 A1 | 6/2014 | Blomquist |
| 2014/0273042 A1 | 9/2014 | Saint |
| 2014/0275419 A1 | 9/2014 | Ward et al. |
| 2014/0276419 A1 | 9/2014 | Rosinko et al. |
| 2014/0276420 A1 | 9/2014 | Rosinko |
| 2014/0276531 A1 | 9/2014 | Walsh |
| 2014/0276553 A1 | 9/2014 | Rosinko et al. |
| 2014/0276556 A1 | 9/2014 | Saint et al. |
| 2014/0276570 A1 | 9/2014 | Saint |
| 2014/0276574 A1 | 9/2014 | Saint |
| 2014/0350371 A1 | 11/2014 | Blomquist et al. |
| 2014/0378898 A1 | 12/2014 | Rosinko |
| 2015/0073337 A1 | 3/2015 | Saint et al. |
| 2015/0182693 A1 | 7/2015 | Rosinko |
| 2015/0182695 A1 | 7/2015 | Rosinko |
| 2015/0217044 A1 | 8/2015 | Blomquist |
| 2015/0314062 A1 | 11/2015 | Blomquist et al. |
| 2016/0082188 A1 | 3/2016 | Blomquist et al. |
| 2016/0199571 A1 | 7/2016 | Rosinko et al. |

FOREIGN PATENT DOCUMENTS

| | | |
|---|---|---|
| DE | 19819407 | 11/1999 |
| DE | 10121317 | 11/2002 |
| DE | 10352456 | 7/2005 |
| EP | 1102194 | 5/2001 |
| EP | 1571582 | 9/2005 |
| JP | 2006034323 | 2/2006 |
| WO | WO0045696 | 8/2000 |
| WO | WO0074753 | 12/2000 |
| WO | WO0152727 | 7/2001 |
| WO | WO02062212 | 8/2002 |
| WO | WO03082091 | 10/2003 |
| WO | WO2005046559 | 5/2005 |
| WO | WO2006/061169 | 6/2006 |
| WO | WO2006127841 | 11/2006 |
| WO | WO2007000425 | 1/2007 |
| WO | WO2007056592 | 5/2007 |
| WO | WO2007089537 | 8/2007 |
| WO | WO2007149533 | 12/2007 |
| WO | WO2008/048582 | 4/2008 |
| WO | WO2008048556 | 4/2008 |
| WO | WO2008048583 | 4/2008 |
| WO | WO2008048584 | 4/2008 |
| WO | WO2008048585 | 4/2008 |
| WO | WO2008048586 | 4/2008 |
| WO | WO2008048587 | 4/2008 |
| WO | WO2008091320 | 7/2008 |

(56) References Cited

FOREIGN PATENT DOCUMENTS

| WO | WO2008/112078 | 9/2008 |
|---|---|---|
| WO | WO2008153689 | 12/2008 |
| WO | WO2008153819 | 12/2008 |
| WO | WO2009016636 | 2/2009 |
| WO | WO 2009/032400 A1 | 3/2009 |
| WO | WO2009035759 | 3/2009 |
| WO | WO2009088983 | 7/2009 |
| WO | WO2009089028 | 7/2009 |
| WO | WO2009089029 | 7/2009 |
| WO | WO2011068648 | 6/2011 |
| WO | WO 2013/016363 A1 | 1/2013 |
| WO | WO2013184896 | 12/2013 |
| WO | WO2013184896 A1 | 12/2013 |

OTHER PUBLICATIONS

Application and File History for U.S. Appl. No. 11/970,232, filed Jan. 7, 2008, inventors Blomquist et al.
Chase et al., "The Use of Insulin Pumps with Meal Bolus Alarms in Children with Type 1 Diabetes to Improve Glycemic Control", Diabetes Care, vol. 29, No. 5, May 2006, pp. 1012-1015.
Walsh, Diabetes Technology—Concept 1: Super Bolus, http://www.diabetesnet.com/diabetes_technology/super_bolus.php> Sep. 17, 2007.
Walsh et al., "Pumping Insulin: Everything You Need for Success On A Smart Insulin Pump" Torrey Pines Press. 2006.
Application and File History for U.S. Appl. No. 12/908,218, filed Oct. 20, 2010, inventors Blomquist et al.
International Preliminary Report and Written Opinion for International Application No. PCT/US2010/056233 dated Jun. 5, 2012.
PCT Search Report dated Aug. 31, 2011 for PCT Application No. PCT/US2010/056233 filed Nov. 10, 2010,
Plougmann et al, "DiasNet-a diabetes advisory system for communication and education via the internet", International Journal of Medical Informatics, vol. 26. pp. 319-330 (2001).
Wilinska et al., "Insulin Kinetics in Type-1 Diabetes: Continuous and Bolus Delivery of Reapid Acting Insulin>" IEEE Transactions on Bopmedical Engineering vol. 52. No. 1, pp. 3-12. Jan. 2005.
Bott et al, "Impact of Smoking on the Metabolic Action of Subcutaneous Regular Insulin in Type 2 Diabetic Patients" Horn. Metab. Res., vol. 37, pp. 445-449 (2005).
Puckett eta l., Am. J. Physiol. vol. 269, p. E1115-E1124, 1995.
Compare Insulin Pump for Diabetes, 4 pages. Printed from www.diabetesnet.com/diabetes_technology/insulin_pump_models.php. Jun. 18, 2009.
Deltec Cozmo. Personalized Insulin Pump. Starting Guide. Internet Article. Smiths Medical. 2004. pp. 1-83. XP002497833.
European Office Action from European Application No. 08779626.4 mailed May 25, 2010.
European Office Action from European Application No. 08767734.6 dated Apr. 7, 2010.
International Search Report for International Application No. PCT/US2007/022050 mailed Mar. 7, 2008.
International Search Report for International Application No. PCT/US09/00107 dated May 4, 2009.
International Search Report for International Application No. PCT/US2007/024424 mailed Mar. 6, 2009.
International Search Report for International Application No. PCT/US2008/002536 dated Sep. 4, 2008.
International Search Report for International Application No. PCT/US2008/006449 mailed Oct. 10, 2008.
International Search Report for International Application No. PCT/US20078/006801 mailed Oct. 30, 2008.
International Search Report for International Application No. PCT/US2009/000034 dated May 27, 2009.
International Search Report for International Application No. PCT/US2009/000106 dated May 13, 2009.
International Search Report from International Application No. PCT/US2007/024423 dated May 19, 2008.
Stapel, Elizabeth, "Converting Between Decimals, Fractions, and Percents", Purplemath. 2006. http://www.purplemath.com/modules/percents2.htm.
Walsh et al., "Select & Test Your Basal Rates", Pumping Insulin, Fourth Edition, Chapter 11/12. (2006).
Walsh et al., "Select & Test Your Correction Factor", Pumping Insulin, Fourth Chapter 13, (2006).
Wikipedia's definition for "basal rate", 1 page. Printed from wikipedia.com.
Written Opinion for International Application No. PCT/US09/00107 dated May 4, 2009.
Written Opinion for International Application No. PCT/US2007/022050 mailed Mar. 7, 2008.
Written Opinion for International Application No. PCT/US2007/024424 mailed Mar. 6, 2009.
Written Opinion for International Application No. PCT/US2008/002536 dated Sep. 4, 2008.
Written Opinion for International Application No. PCT/US2008/006449 dated Oct. 10, 2008.
Written Opinion for International Application No. PCT/US2008/006801 mailed Oct. 30, 2008.
Written Opinion for International Application No. PCT/US2009/000034 dated May 27, 2009.
Written Opinion for International Application No. PCT/US2009/000106 dated May 13, 2009.
Written Opinion from International Application No. PCT/US2007/024423 dated May 19, 2008.
International Search Report for International Application No. PCT/US2007/022046 dated Mar. 7, 2008.
Written Opinion for International Application No. PCT/US2007/022046 dated Mar. 7, 2008.
Trajanoski et al., Pharmacokinetic Model for the Absorption Subcutaneoutsly Injected Soluble Insulin and Monomeric Insulin Analogues. Biomedizinische Technik,. vol. 38 No. 9. Sep. 1, 1993.
Hildebrandt, Subcutaneous Absorption of Insulin in Insulin-Dependent Diavetic patients. Influence of Species Physico-Chemcial properties of Insulin and Physiological factors. Danish Medical Bulletin. Aug. 1991.
Written Opinion for International Application No. PCT/US2007/022004 dated Oct. 9, 2008.
International Search Report for International Application No. PCT/US2007/022004 dated Oct. 9, 2008.
Written Opinion for International Application No. PCT/US2007/022047 dated Mar. 7, 2008.
International Search Report for International Application PCT/US2007/022047 dated Mar. 7, 2008.
Written Opinion for International Application No. PCT/US2007/022048 dated Mar. 7, 2008.
International Search Report for International Application No. PCT/US2007/022048 dated Mar. 7, 2008.
Written Opinion for International Application No. PCT/US2007/022049 dated Mar. 7, 2008.
International Search Report for International Application No. PCT/US2007/022049 dated Mar. 7, 2008.
International Search Report for International Application No. PCT/US2007/022051 dated Mar. 7, 2008.
Written Opinion for International Application No. PCT/US2007/022051 mailed Mar. 7, 2008.
International Search Report for International Application No. PCT/US2007/022052 dated May 11, 2007.
Written Opinion for International Application No. PCT/US2007/022052 mailed May 11, 2007.
European Office Action from European Application No. 07852760.3 dated Aug. 11, 2010.
Application and File History for U.S. Appl. No. 13/481,302, filed May 25, 2012, inventors Blomquist et al.
Application and File History for U.S. Appl. No. 14/797,652, filed Jul. 13, 2015, inventors Blomquist et al.
Lehman et al., "Artificial Intelligence in Medicine" vol. 6. pp. 137-160. 1994.
Wach et al., Med & Biol. Eng & Comput. vol. 33 pp. 18-23. 1995.
Search Report and Written Opinion dated May 7, 2014 for PCT Application No. PCT/US2014/021318.

(56) References Cited

OTHER PUBLICATIONS

Application and File History for U.S. Appl. No. 14/962,635, filed Dec. 8, 2015, inventors Blomquist et al.
Application and File History for U.S. Appl. No. 14/187,414, filed Feb. 24, 2014, inventors Blomquist.
IPRP and Written Opinion for International Application No. PCT/US2010/056226 dated Jun. 14, 2012.
Canadian Office Action for Canadian Application No. 2,782,673 dated Sep. 10, 2013.
Japanese Office Action for Japanese Application No. 2012542037 dated Sep. 2, 2014. English translation not available.
Chinese Office Action for Chinese Application No. 201080063326.9 dated Jan. 27, 2014. English translation not available.
European Search Report for European Application No. 15168432 completed Sep. 1, 2015 and mailed Sep. 8, 2015.
International Search Report and Written Opinion for International Application No. PCT/US2014/021109 dated Jun. 5, 2014.
International Search Report and Written Opinion for International Application No. PCT/US2015/042881 dated Nov. 11, 2015.
Application and File History for U.S. Appl. No. 11/685,617, filed Mar. 13, 2007, inventors Blomquist et al.
Application and File History for U.S. Appl. No. 13/842,005, filed Mar. 15, 2013, inventors Saint et al.
Application and File History for U.S. Appl. No. 13/800,453, filed Mar. 13, 2013, inventors Rosinko et al.
Application and File History for U.S. Appl. No. 14/455,508, filed Aug. 8, 2014, inventors Blomquist et al.

* cited by examiner

TEMPORARY SUSPENSION FOR CLOSED-LOOP MEDICAMENT THERAPY

RELATED APPLICATION

The present application claims the benefit of U.S. Provisional Application No. 62/030,933 filed Jul. 30, 2014, which is incorporated herein in its entirety by reference.

FIELD OF THE INVENTION

The present invention relates to closed-loop therapy for delivery of medicament such as insulin to a user and, more particularly, to temporary suspension of closed-loop therapy when patient behavior may interfere with the accuracy and efficacy of the therapy.

BACKGROUND OF THE INVENTION

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of pumps that have been developed for the administration of insulin and other medicaments for those suffering from both type I and type II diabetes. Some pumps configured as portable infusion devices can provide continuous subcutaneous medicament injection and/or infusion therapy for the treatment of diabetes. Such therapy may include, e.g., the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. patent application Ser. Nos. 13/557,163, 12/714,299, 12/538,018, 13/838,617, 13/827,707 and U.S. Pat. Ser. No. 8,287,495, each of which is hereby incorporated herein by reference in its entirety.

Portable infusion pumps for delivering insulin or other medicaments can be used in conjunction with continuous glucose monitoring (CGM) devices. A CGM provides a substantially continuous estimated blood glucose level through a transcutaneous sensor that measures analytes, such as glucose, in the patient's interstitial fluid rather than the patient's blood. CGM systems typically consist of a transcutaneously-placed sensor, a transmitter and a monitor. A CGM system allows a patient or caregiver to insert a single sensor probe under the skin for multiple days. Thus, the patient is only required to perform a single moderately invasive action with a single entry point in the subdermal layer on, e.g., a weekly basis.

Ambulatory infusion pumps typically allow the patient or caregiver to adjust the amount of insulin or other medicament delivered, by a basal rate or a bolus, based on blood glucose data obtained by a blood glucose meter (BGM) or a CGM. Some ambulatory infusion pumps may include the capability to interface with a BGM or CGM such as, e.g., by receiving measured or estimated blood glucose levels and prompting the patient or caregiver to adjust the level of medicament being administered or planned for administration or, in cases of abnormally low blood glucose readings, prompting temporary cessation of insulin administration. These portable pumps may incorporate a BGM or CGM within the hardware of the pump or may communicate with a dedicated BGM or CGM via wired or wireless data communication protocols. Such pumps may be particularly important in facilitating patient compliance and improved or more accurate treatment of diabetes. One example of integration of infusion pumps with CGM devices is described in U.S. Patent Application No. 2014/0276419, which is hereby incorporated by reference herein.

The delivery of insulin or other medicament from a portable infusion pump making use of CGM data necessitates accurate and reliable CGM data output. CGM devices are therefore calibrated with blood samples to correlate actual blood glucose data with the CGM readings. However, such calibrations are only done periodically, such as every 12 hours, and the longer it has been since a calibration the more likely the CGM is unreliable to some degree and the more unreliable the CGM is likely to become until the next calibration.

Insulin or other medicament dosing by basal rate and/or bolus techniques could automatically be provided by a pump based on readings received into the pump from a CGM device that is, e.g., external to the portable insulin pump or integrated with the pump as a pump-CGM system in a closed-loop fashion. With respect to insulin delivery, some systems including this feature are sometimes referred to as artificial pancreas systems because the systems serve to mimic biological functions of the pancreas for patients with diabetes. However, there are a number of risks in automatically dosing insulin, or other medicaments, based on CGM readings that can become inaccurate or unreliable. For example, a CGM reading or readings may indicate that a user's blood glucose level is high and therefore the pump may automatically deliver a bolus of medicament or increase the basal rate to lower the user's blood glucose to a target level. However, if the CGM reading is inaccurately high, the extra medicament may actually lower the user's blood glucose below a desired target level, possibly to a dangerously low level. Thus, automatically dosing medicaments such as insulin based on CGM readings can have potentially dangerous effects in situations where the CGM readings are inaccurate relative to the user's actual blood glucose levels.

SUMMARY OF THE INVENTION

A portable infusion pump can communicate with a continuous glucose monitor (CGM) to receive continuous feedback relating to a patient's blood glucose level during insulin or other medicament therapy and can automatically deliver insulin to a user when the CGM data indicates a need for additional insulin. Because patient behavior or events affecting the patient can interfere with the accuracy and efficacy of such closed loop or semi-closed loop therapy, a system can employ various mechanisms for manual temporary suspension of closed-loop therapy when a patient, caregiver, or other user is aware that current or future behavior may inhibit therapy.

In some embodiments, a portable infusion pump system that provides closed loop or semi-closed loop therapy based on information from a continuous glucose monitor employs a temporary suspension feature based on medication taken by a patient. Certain medications will cause or likely cause readings from the CGM sensor to become unreliable. When the patient is going to take or has taken such a medication, the patient, caregiver, or other user can access a temporary suspend feature to provide an indication to the system of the ingestion of such a medication. The system can then suspend closed loop therapy based on the CGM data and deliver medicament according to a default delivery pattern for a suspension period. Following the suspension period, the system can resume utilizing the CGM data to deliver closed loop therapy. In various embodiments, the suspension period can be manually entered by the user, a default value or calculated by the system based on, e.g., the type of medication, dosage, etc.

In some embodiments, a portable infusion pump system that provides closed loop or semi-closed loop therapy based on information from a continuous glucose monitor employs a temporary suspension feature based on other or additional patient behaviors or events affecting the patient that may affect the efficacy of therapy. Such behaviors can include, for example, excessive food consumption, such as at a buffet (i.e., binge eating), excessive alcohol consumption (i.e. binge drinking), excessive exercise (e.g., a marathon) and illness. When a user is aware that the patient is going to engage in such an activity or be subjected to such an event, the user can access the suspend function of the system to suspend the CGM based therapy functions and the system can revert to a default medicament delivery schedule for a suspension period.

Certain embodiments are described further in the following description, examples, claims, and drawings. These embodiments will become more apparent from the following detailed description when taken in conjunction with the accompanying exemplary drawings.

DETAILED DESCRIPTION OF THE DRAWINGS

Figure 1:
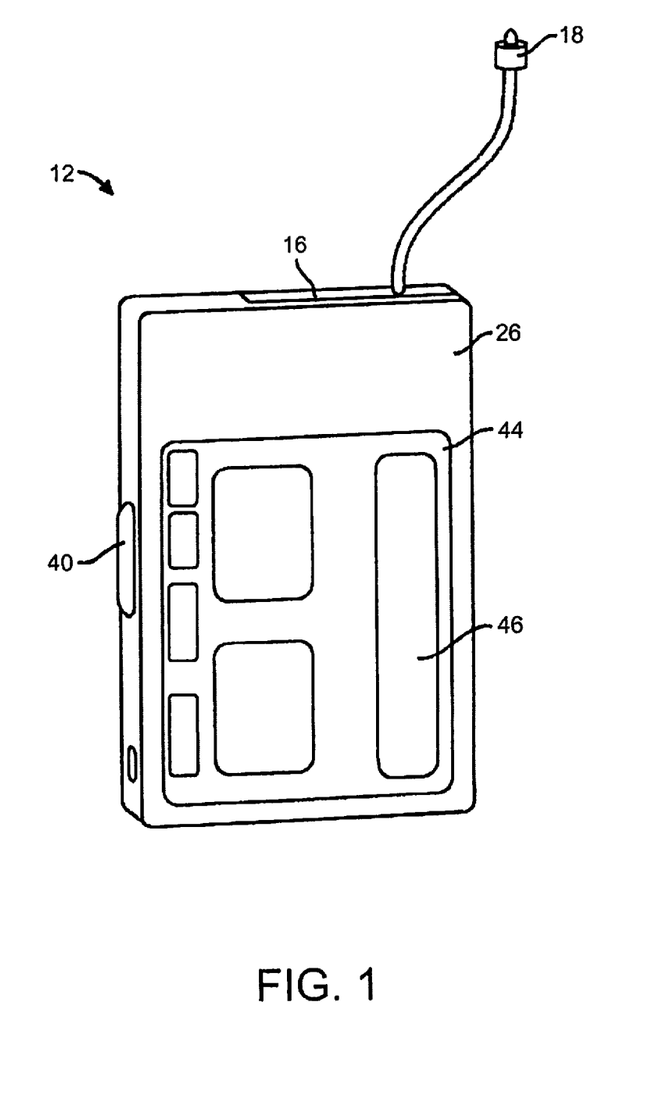
FIG. 1 is a perspective view of an infusion pump according to an embodiment of the present invention.

FIG. 1 depicts an embodiment of a medical device that can be used with embodiments of the present invention. In this embodiment, the medical device is configured as a pump 12, such as an infusion pump, that can include a pumping or delivery mechanism and reservoir for delivering medicament to a patient and an output/display 44. The type of output/display 44 may vary as may be useful for a particular application. When visual, output/display 44 may include LCD displays, LED displays, plasma displays, graphene-based displays, OLED displays and the like. The output/display 44 may include an interactive and/or touch sensitive screen 46 having an input device such as, for example, a touch screen comprising a capacitive screen or a resistive screen. The pump 12 may additionally include a keyboard, microphone, or other input device known in the art for data entry, which may be separate from the display. The pump 12 may also include a capability to operatively couple to a secondary display device such as a remote display, a remote control device, a laptop computer, personal computer, tablet computer, mobile communication device such as a smartphone or personal digital assistant (PDA), or the like.

In one embodiment, the medical device can be a portable insulin pump configured to deliver insulin to a patient. Further details regarding such pump devices can be found in U.S. Patent Publication No. 2011/0144586, which is incorporated herein by reference in its entirety. In other embodiments, the medical device can be an infusion pump configured to deliver one or more additional or other medicaments to a patient. In a further embodiment, the medical device can be a glucose meter such as a continuous glucose monitor. Further detail regarding such systems and definitions of related terms can be found in, e.g., U.S. Pat. Nos. 8,311,749, 7,711,402 and 7,497,827, each of which is hereby incorporated by reference herein in its entirety. In other embodiments, the medical device can monitor other physiological parameters of a patient.

Figure 2:
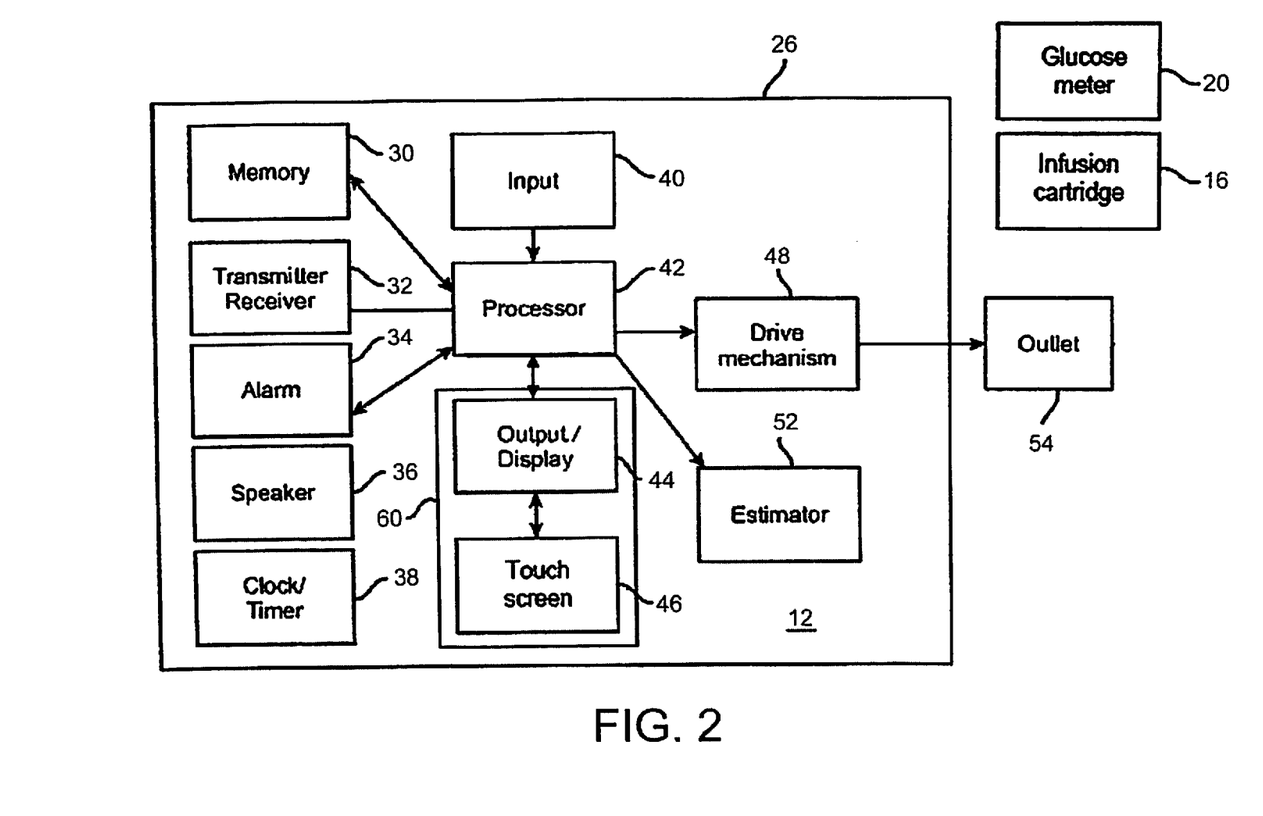
FIG. 2 is a block diagram representing an embodiment of an infusion pump according to the present invention.

FIG. 2 illustrates a block diagram of some of the features that can be sued with embodiments of the present invention, including features that may be incorporated within the housing 26 of a medical device such as a pump 12. The pump 12 can include a processor 42 that controls the overall functions of the device. The infusion pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured).The housing 26 of the pump 12 may be functionally associated with an interchangeable and removable glucose meter 20 or infusion cartridge 16. The infusion cartridge 16 may have an outlet port 54 that may be connected to an infusion set connector 18 and an infusion set. One embodiment of a user interface as shown in FIG. 2 is a graphical user interface (GUI) 60 having a touch sensitive screen 46 with input capability. In some embodiments, the processor 42 may communicate with one or more other processors within the pump 12 and/or one or more processors of other devices, for example, a continuous glucose monitor (CGM), display device, smartphone, etc. through the transmitter/receiver. The processor 42 may also include programming that may allow the processor to receive signals and/or other data from an input device, such as a sensor that may sense pressure, temperature or other parameters.

Figure 3:
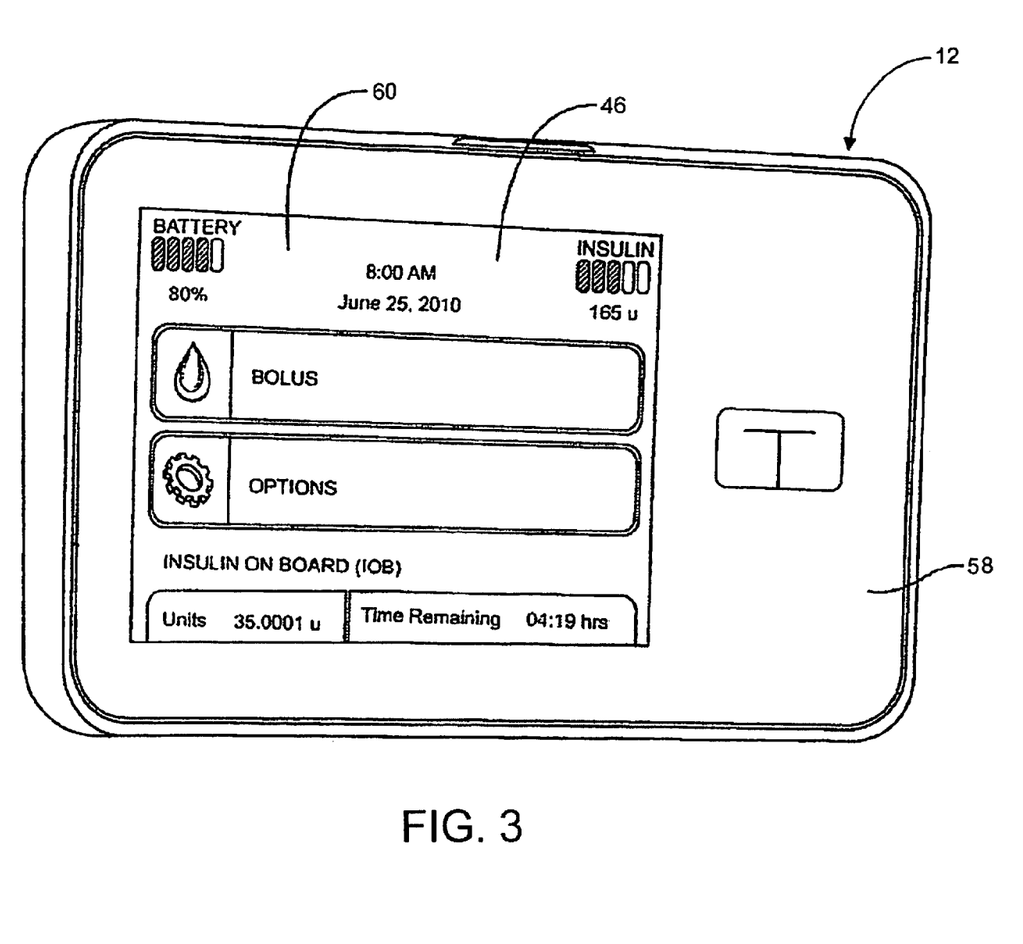
FIG. 3 depicts a screen shot of a home screen page of a graphical user interface of an infusion pump according to an embodiment of the present invention.

Referring to FIG. 3, a front view of pump 12 is depicted. Pump 12 may include a user interface, such as, for example, a GUI 60 on a front surface 58 or other location of pump 12. GUI 60 may include a touch-sensitive screen 46 that may be configured for displaying data, facilitating data and/or command entry, providing visual tutorials, as well as other interface features that may be useful to a caregiver or to the patient operating pump 12. The GUI can also present alarms or alerts to the user.

Figure 4:
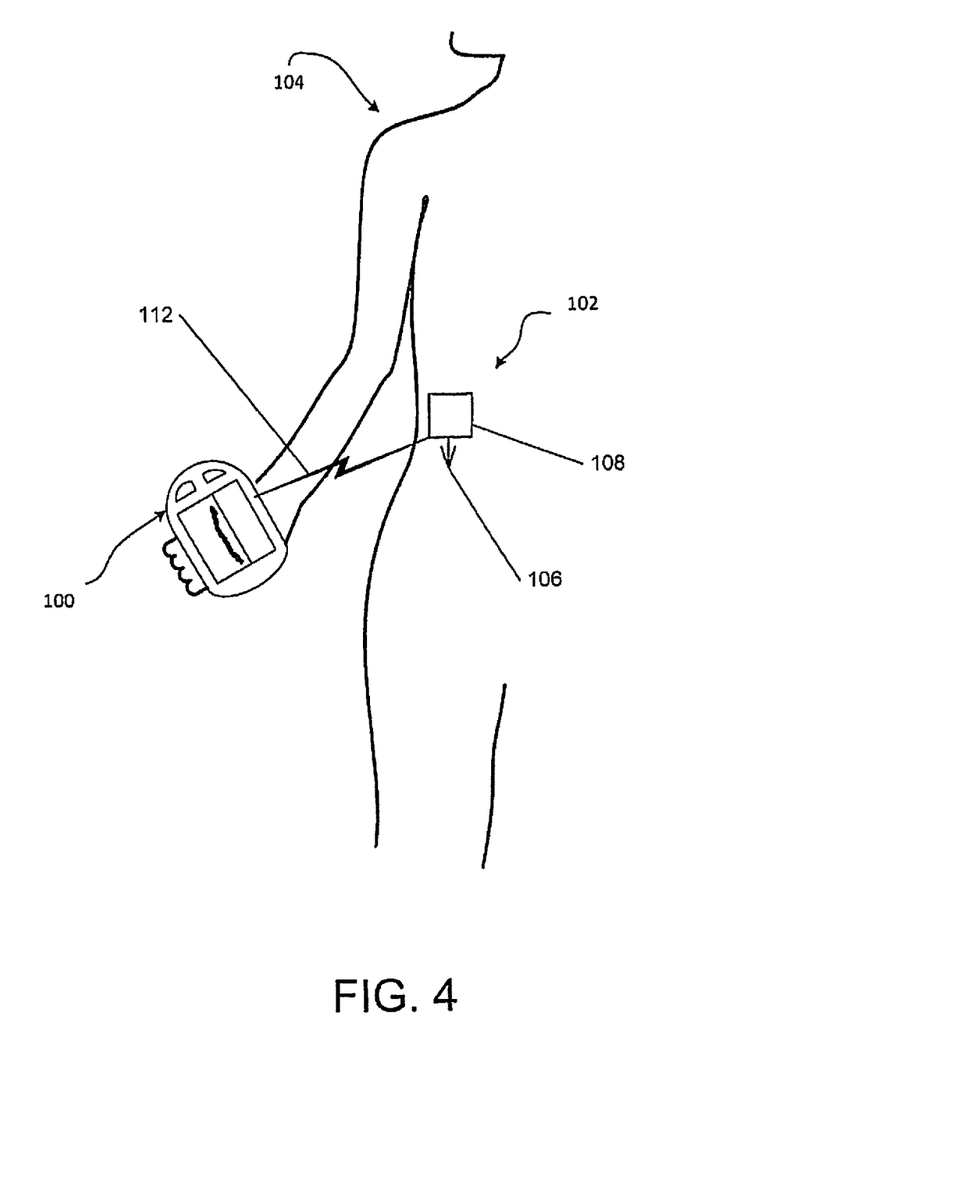
FIG. 4 is a partial schematic view depicting a continuous glucose monitor according to an embodiment of the present invention that may, e.g., be deployed on a patient.

Pump 12 can interface with a glucose meter, such as a continuous glucose monitor (CGM), that provides a substantially continuous estimated glucose level through a transcutaneous sensor that measures analytes, such as glucose, in the patient's interstitial fluid rather than the patient's blood. Referring to FIG. 4, an exemplary CGM system 100 according to an embodiment of the present invention is shown (other CGM systems can be used). The illustrated CGM system 100 includes a sensor 102 affixed to a patient 104 and is associated with the infusion device 12. The sensor 102 includes a sensor probe 106 configured to be inserted to a point below the dermal layer (skin) of the patient 104. The sensor probe 106 is therefore exposed to the patient's interstitial fluid or plasma beneath the skin and reacts with that interstitial fluid to produce a signal that can be calibrated with the patient's blood glucose (BG) level. The sensor 102 includes a sensor body 108 that transmits data associated with the interstitial fluid to which the sensor probe is exposed. The data may be transmitted from the sensor 102 to the glucose monitoring system 100 via a wireless transmitter, such as a near field communication (NFC) radio frequency (RF) transmitter or a transmitter operating according to a "Wi-Fi" or Bluetooth® protocol or the like, or the data may be transmitted via a wire connector from the sensor 102 to the monitor system 100. Transmission of sensor data to the glucose monitor system 100 by wireless or wired connection is represented in FIG. 4 by the arrow line 112. Further detail regarding such systems and definitions of related terms can be found in, e.g., U.S. Pat. Nos. 8,311,749, 7,711,402 and 7,497,827, each of which is hereby incorporated by reference in its entirety.

In one embodiment, part of the CGM system 100 is incorporated into the pump 12 such that the processor 42 is adapted to receive the data from the sensor 102 and process and display the data on the display 44. In another embodiment, the CGM 100 is a separate device that communicates with the pump 12 through a wired or wireless link to transmit the CGM data to the pump 12.

In an embodiment of a pump 12 that communicates with a CGM and that integrates CGM data and pump data as described herein, the CGM can automatically transmit the glucose data to the pump. The pump can then automatically determine therapy parameters based on the data. For example, if the CGM data indicates that the user's blood glucose level is over a high blood glucose threshold level stored in memory, the pump can automatically calculate an insulin or other medicament bolus amount or an increase to a basal rate to bring the user's blood glucose level below the threshold or to a target value. As with other parameters related to therapy, such thresholds and target values can be stored in memory located in the pump or, if not located in the pump, stored in a separate location and accessible by the pump processor (e.g., "cloud" storage accessible via a network connection). The pump processor can periodically and/or continually execute instructions for a checking function that accesses this data in memory, compares it with data received from the CGM and acts accordingly.

In one embodiment, such an automatic system for insulin delivery is referred to as an artificial pancreas system that provides closed loop or semi-closed loop therapy to the patient that mimics the natural functions of a healthy pancreas. In such a system, insulin doses are calculated based on the CGM readings and are automatically delivered to the patient at least in part based on the CGM reading(s). For example, if the CGM indicates that the user has a high blood glucose level or hyperglycemia, the system can calculate an insulin dose necessary to reduce the user's blood glucose level below a threshold level or to a target level and automatically deliver the dose. Alternatively, the system can automatically suggest a change in therapy such as an increased insulin basal rate or delivery of a bolus, but can require the user to accept the suggested change prior to delivery. If the CGM data indicates that the user has a low blood glucose level or hypoglycemia, the system can, for example, automatically reduce a basal rate, suggest to the user to reduce a basal rate, automatically deliver or suggest that the user initiate the delivery of an amount of a substance such as, e.g., a hormone (glucagon) to raise the concentration of glucose in the blood, suggest that the user, e.g., ingest carbohydrates and/or automatically take other actions and/or make other suggestions as may be appropriate to address the hypoglycemic condition, singly or in any desired combination or sequence. Such determination can be made by the infusion pump providing therapy or by a separate device that transmits therapy parameters to the infusion pump. In some embodiments, multiple medicaments can be employed in such a system as, for example, a first medicament, e.g., insulin, amylin/pramlintide, etc. that lowers blood glucose levels and a second medicament, e.g., glucagon, that raises blood glucose levels.

Because such artificial pancreas systems that incorporate CGM data automatically to adjust insulin therapy in a closed-loop fashion rely on the CGM data to be reliable, it may be desirable to implement various features to, e.g., ensure the safety of the patient. Embodiments of the present invention therefore incorporate a temporary suspend feature for artificial pancreas and any other systems that provide closed-loop or semi-closed-loop therapy in which CGM data is relied upon, in whole or in part, automatically to determine dosing information.

Figure 5:
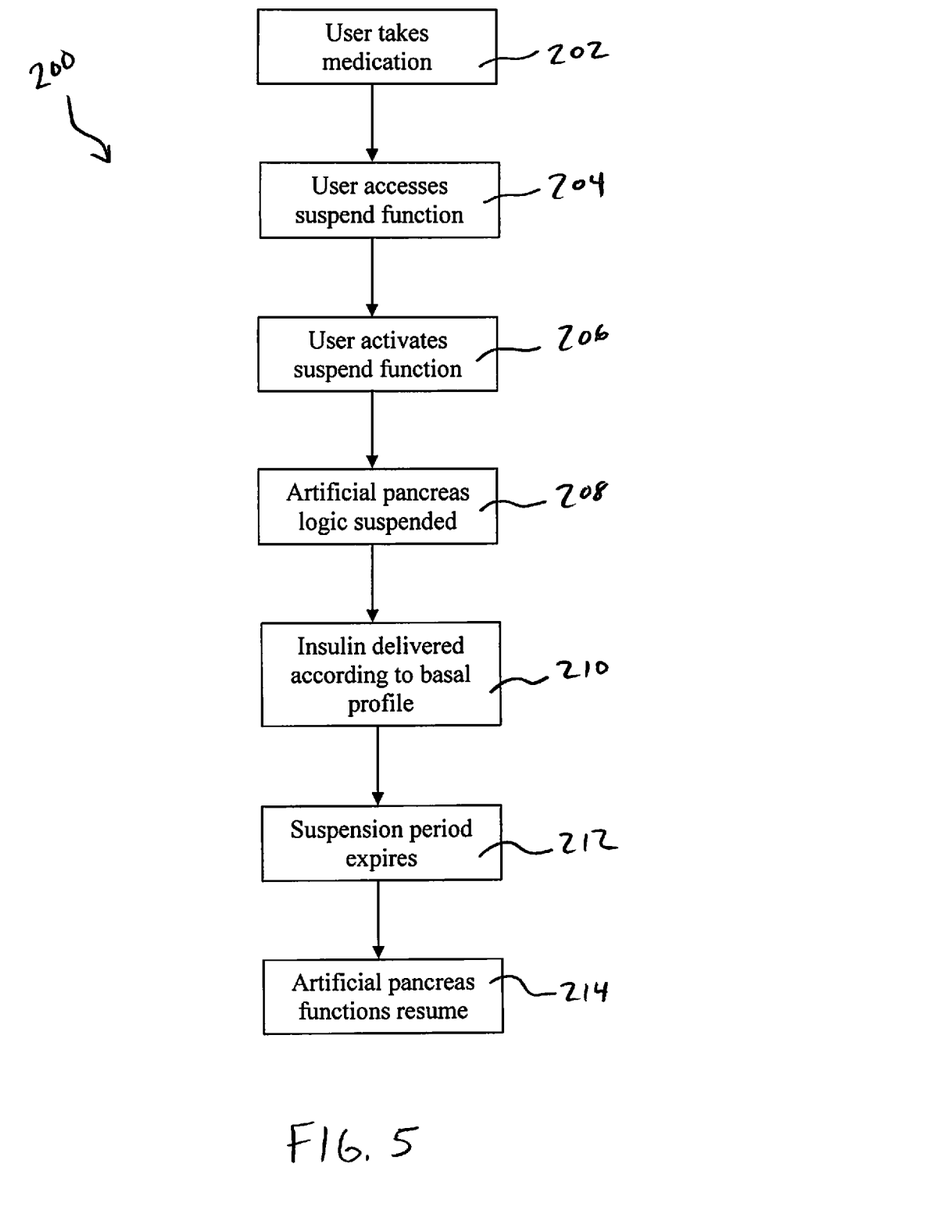
FIG. 5 is a flowchart of a method of temporarily suspending closed-loop delivery of medicament according to an embodiment of the present invention.

In one embodiment, a user such as a patient, caregiver, or other having access to the pump can manually select temporarily to suspend automatic adjustment of insulin or other medicament therapy based on CGM data when the user knows that the CGM data may be or may become unreliable. For example, certain medications will cause or likely cause readings from the CGM sensor to become unreliable. FIG. 5 sets forth one embodiment of a method 200 in which a user temporarily suspends utilization of closed-loop therapy such as therapy driven by artificial pancreas logic by an insulin pump. At step 202, a patient takes a medication that is known to cause or be likely to cause CGM sensor readings to be unreliable. The user at step 204 can then access a suspend function of the system. The function can be accessed through, for example, a user interface of the insulin pump or a smart phone or other remote device that is wirelessly connected to the pump. The user activates the suspend function at step 206. Activation of the suspend function causes the artificial pancreas or other logic driving the closed-loop therapy to be suspended at step 208. As an example of what suspension step 208 may include, in one embodiment step 208 would require that insulin is instead automatically delivered according to a set basal profile of the patient stored on the pump at step 210. Upon conclusion of the suspension period at step 212, artificial pancreas or other closed-loop functions can automatically be resumed at step 214. In some embodiments, the patient or caregiver can be notified on, e.g., a user interface of the pump or a smartphone, that closed-loop therapy functions have resumed. Alternatively, the user can be prompted as to whether to resume closed-loop therapy functions after the suspension period.

The length of the suspension period can vary based on, e.g., the type of drug and dosage taken or anticipated to be taken by the patient and the set basal profile that will be utilized during the suspension period. In some embodiments, the length of the suspension period can be entered by the user. In other embodiments, the pump can store in memory or have access to a database of drugs and the user can enter the drug taken and dosage information and the system can automatically calculate a suspension period based on a comparison of the entered information to the database and/or additional information that may or may not be in the database and may be entered by the patient or a caregiver, such as, e.g. , the age of the patient, the weight of the patient, the sex of the patient, whether the patient is taking other medications(s), and if so, the other medication's type, dosage amount, time of ingestion, mode of ingestion, as well as other information together or in combination with the aforementioned factors that may inform the proper suspension period.

As a specific example, a patient may take acetaminophen for a headache, which the user knows will be likely to cause unreliably high glucose readings from the CGM sensor. The user may enter a suspension period of, e.g., three hours, or the pump may determine, based on any number of factors, that an appropriate suspension period for a dose of acetaminophen is three hours. Over that suspension period, the pump delivers insulin according to a set basal profile without modifications from the artificial pancreas or other closed-loop therapy logic. At the conclusion of the three hours, the closed-loop therapy functions resume, either automatically or after prompting the user.

In certain embodiments, all closed-loop therapy modifications to insulin delivery are disabled during the suspension period. Alternatively, only a portion of the closed-loop functions can be disabled. For example, if the medication is known potentially to cause high glucose readings, only high glucose corrections may be suspended in order to protect against hypoglycemia due to unreliable sensor readings but not inhibit necessary corrections based on low glucose readings. Similarly, if the medication is known to be likely to cause low readings, only low glucose corrections can be suspended. In addition, in embodiments delivering more than one medicament, such as two medicaments, the suspension can be applied to any number of the medicaments, such as one of the medicaments or both of the medicaments, and can be applied differently, e.g., for different time periods, for each medicament. Suspension of only a portion of closed-loop therapy functions can be manually determined by the user or can be automatically selected by the pump based on entered drug information.

It should be noted that while an embodiment of the invention is described as implementing a temporary suspension of artificial pancreas functions due to medication taken by the user being likely to cause inaccurate or unreliable CGM readings, one skilled in the art will understand that artificial pancreas or other closed-loop therapy functions can be temporarily suspended if the CGM is likely to be inaccurate or unreliable for any other reason, such as, for example, the CGM has not been calibrated within a threshold period of time. Similarly, temporary suspension can be available for reasons other than likely CGM data inaccuracy or unreliability.

For example, temporary suspension can be implemented to account for other non-typical patient behaviors or events that may cause the artificial pancreas algorithms to become ineffective due to extreme effects on the user's blood glucose levels. These non-typical behaviors can include, for example, excessive food consumption, such as at a buffet (i.e., binge eating), excessive alcohol consumption (i.e. binge drinking), excessive exercise (e.g., running a marathon), and other events or occurrences that may not be related to a patient's behavior such as illness, injury, shock, etc. Any number of other non-typical behaviors and/or events or occurrences other than those listed herein are contemplated for purposes of the embodiments and methods disclosed herein. When a user, such as a patient or caregiver, is aware that a patient is going to engage in such an activity or be subject to such an event, the user can access the suspend function system to suspend the artificial pancreas functions. The system can then revert to a default medicament delivery schedule or medicament can be manually administered by the user during the suspension period.

In one embodiment, temporary suspend function can be provided generically to turn on and off for any reason, with no further information provided by the user. In other embodiments, the described temporary suspend function can be activated specifically because the user indicates to the system that a non-typical patient behavior or event that may affect reliability of CGM data will be or is being engaged in. In further embodiments, the user can indicate the specific non-typical behavior, e.g., binge drinking, to the system. Artificial pancreas functions can, for example, remain suspended indefinitely until a user turns them back on, remain suspended for a period of time entered by the user upon activation of the suspend function, remain suspended for a predefined suspension period stored in memory for all non-typical user behaviors/events, or remain suspended for a predefined suspension period stored in memory for a specific indicated non-typical behavior/event. As to the latter embodiment, in some embodiments a user can provide an estimate of additional information regarding the non-typical activity or event, e.g., number of carbohydrates to be consumed, number of drinks, amount of time of activity, etc. and the suspension period can be calculated based on the additional information. Following the suspension period, in certain embodiments the artificial pancreas functions can automatically resume or can resume following a user confirmation in response to a prompt to the user that the suspension period has ended and asking whether artificial pancreas functions should be resumed.

Although the embodiments of the invention discussed above are primarily described as temporarily suspending artificial pancreas functions in response to an express indication from a user of a patient behavior, activity, etc. that may cause the CGM data to become unreliable, it is within the scope of the present invention for the system itself, through, for example, processor 42 of the pump 12 or an external processor, to determine that such unreliability is likely and enact a temporary suspension. For example, such a system can include any number of sensors or other devices to measure patient characteristics. Such devices can include, for example, an accelerometer or other motion sensor and a heart rate monitor.

In one such embodiment, the system can monitor data from an accelerometer. If the accelerometer data indicates that the patient has been exercising or otherwise moving at a higher than normal rate for a certain (e.g.) extended period of time, the system can determine that closed loop therapy functions should be temporarily suspended. This determination can be made based on the accelerometer data exceeding a threshold level stored in memory. Such a threshold can be a value determined to correlate such data with, e.g., an increased caloric burn rate that would necessitate enacting of a temporary suspension period. Similarly, if a heart rate monitor indicates that a heart rate of the patient has exceeded a threshold or has exceeded (the same or a lower) threshold for a predetermined period of time, the system can determine that a temporary suspension period should be enacted.

A system-determined suspension, for any of the embodiments described herein, can be enacted and lifted in various ways. In some embodiments, the system can automatically suspend closed loop therapy functions, with or without a notification to a user. Alternatively, the system can provide a prompt to the user indicating that the system has determined that a temporary suspension is appropriate but require a confirmation from a user before enacting the suspension. Such a confirmation can include, for example, an affirmative confirmation or a predetermined period of time passing without the user declining the suspension. Similarly, following the suspension period, which, as discussed above, can be, for example, calculated by the system, a default value, or entered by a user, the system can automatically resume closed loop therapy functions, with or without a notification to the user or can be resumed only after prompting the user whether to resume therapy based on the CGM data.

Although embodiments herein may be specifically described with respect to the delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 8,287,495; 8,408,421; 8,448,824; 8,573,027; 8,650,937; and 8,986,253, commonly owned U.S. Patent Publication Nos. 2009/0287180; 2012/0123230; 2013/0053816; 2013/0159456; 2013/0276423; 2013/0283196 2013/0306191; 2013/0324928; 2013/0331778; 2013/0331790; 2013/0332874; 2014/0273042; 2014/0276409; 2014/0276531; 2014/0276419; 2014/0276420; 2014/0276538; 2014/0276537; 2014/0276553; 2014/0276556; 2014/0276569; 2014/0276570; 2014/0276571; 2014/0276574; 20140378898; 2015/0072613; 2015/0073337; 2015/0182693; 2015/0182694 and 2015/0182695 commonly owned U.S. patent application Ser. Nos. 14/707,851 and commonly owned U.S. Provisional Application Serial Nos. 61/911,576, 62/030,933 and 62/163,158.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519 ; 6,641,533; 6,554,798; 6,551,276; 6,295,506; and 5,665,065.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. An infusion pump system, comprising:
a delivery mechanism adapted to facilitate delivery of medicament to a patient;
memory adapted to store parameters relating to the delivery of medicament;
a communications device adapted to receive information from a continuous glucose monitor; and
a processor functionally linked to the delivery mechanism and the memory and to the communications device to obtain the information from the continuous glucose monitor, the processor configured to:
cause the delivery mechanism to deliver medicament to the patient according to therapy parameters determined based on the information from the continuous glucose monitor;
determine from user-defined input that the patient is going to take or has taken a medication;
suspend delivery of medicament according to the determined therapy parameters for a suspension period in response to the determination that the patient is going to take or has taken a medication;
cause the delivery mechanism to deliver medicament according to a default medicament delivery schedule stored in memory during the suspension period; and
resume causing the delivery mechanism to deliver medicament to the patient according to the determined therapy parameters following the suspension period, and
wherein the processor is further configured to receive a duration for the suspension period entered through a user interface in communication with the processor.

2. The portable infusion pump of claim 1, wherein the processor is further configured to receive an indication of a type of medication the patient is going to take or has taken.

3. The portable infusion pump of claim 2, wherein the processor is further configured to determine whether the type of medication is one likely to cause the information from the continuous glucose monitor to become unreliable, and suspend delivery of the medicament only if the type of medication is one likely to cause the information from the continuous glucose monitor to become unreliable.

4. The portable infusion pump of claim 1, wherein the processor is configured to resume causing the delivery mechanism to deliver medicament to the patient according to the determined therapy parameters automatically following the suspension period.

5. The portable infusion pump of claim 1, wherein the processor is further configured to provide a prompt on the user interface in communication with the processor that the suspension period has ended and to resume causing the delivery mechanism to deliver the medicament to the patient according to the determined therapy parameters following the suspension period only after receiving a confirmation in response to the prompt.

6. The portable infusion pump of claim 1, wherein the processor is configured to determine the therapy parameters based on the information from the continuous glucose monitor.

7. An infusion pump system, comprising:
a delivery mechanism adapted to facilitate a delivery of a medicament to a patient;
a memory adapted to store parameters relating to the delivery of the medicament;
a communications device adapted to receive information from a continuous glucose monitor; and
a processor functionally linked to the delivery mechanism and the memory and to the communications device to obtain the information from the continuous glucose monitor, the processor configured to:
cause the delivery mechanism to deliver the medicament to the patient according to therapy parameters determined based on the information from the continuous glucose monitor;
determine from user-defined input that the patient is going to take or has taken a medication;
suspend delivery of the medicament according to the determined therapy parameters for a suspension period in response to the determination that the patient is going to take or has taken a medication;
cause the delivery mechanism to deliver the medicament according to a default medicament delivery schedule stored in the memory during the suspension period; and
resume causing the delivery mechanism to deliver the medicament to the patient according to the determined therapy parameters following the suspension period, and
wherein the processor is further configured to receive an indication of the type of the medication the patient is going to take or has taken and determine a duration for the suspension period based on the type of the medication.

8. The portable infusion pump of claim 7, wherein the processor additionally determines the duration for the suspension period based at least in part on a dosage size of the medication.

9. The portable infusion pump of claim 7, wherein the processor is further configured to determine whether the type of the medication is on likely to cause the information from the continuous glucose monitor to become unreliable, and suspend delivery of the medicament only if the type of the medication is one likely to cause the information from the continuous glucose monitor to become unreliable.

10. The portable infusion pump of claim 7, wherein the processor is configured to resume causing the delivery mechanism to deliver the medicament to the patient according to the determined therapy parameters automatically following the suspension period.

11. The portable infusion pump of claim 7, wherein the processor is further configured to provide a prompt a user interface in communication with the processor that suspension period has ended and to resume causing the delivery mechanism to deliver the medicament to the patient according to the determined therapy parameters following the suspension period only after receiving a confirmation in response to the prompt.

12. The portable infusion pump of claim 7, wherein the processor is configured to determine the therapy parameters based on the information from the continuous glucose monitor.

13. An infusion pump system, comprising:
a delivery mechanism adapted to facilitate a delivery of a medicament to a patient;
a memory adapted to store parameters relating to the delivery of the medicament;
a communications device adapted to receive information from a continuous glucose monitor; and
a processor functionally linked to the delivery mechanism and the memory and to the communications device to obtain the information from the continuous glucose monitor, the processor configured to:
cause the delivery mechanism to deliver the medicament to the patient according to therapy parameters determined based on the information from the continuous glucose monitor;
receive an indication that the patient is going to take or has taken a medication;
suspend delivery of the medicament according to the determined therapy parameters for a suspension period in response to the indication;
cause the delivery mechanism to deliver the medicament according to a default medicament delivery schedule stored in the memory during the suspension period; and
resume causing the delivery mechanism to deliver the medicament to the patient according to the determine therapy parameters following the suspension period,
wherein the processor is further configured to receive an indication of a type of medication the patient is going to take or has taken, and
wherein the processor is further configured to determine whether the type of medication is one likely to cause the information from the continuous glucose monitor to become unreliable, and suspend delivery of the medicament only if the type of medication is one likely to cause the information from the continuous glucose monitor to become unreliable.

14. The portable infusion pump of claim 13, wherein the processor is further configured to receive a duration for the suspension period entered through a user interface in communication with the processor.

15. The portable infusion pump of claim 13, wherein the processor is further configured to determine a duration for the suspension period based on the type of medication.

16. The portable infusion pump of claim 15, wherein, the processor additionally determines the duration for the suspension period based at least in part on a dosage size of the medication.

17. The portable infusion pump of claim 13, wherein the processor is configured to resume causing the delivery mechanism to deliver the medicament to the patient according to the determined therapy parameters automatically following the suspension period.

18. The portable infusion pump of claim 13, wherein the processor is further configured to provide a prompt on a user interface in communication with the processor that the suspension period has ended and to resume causing the delivery mechanism to deliver the medicament to the patient according to the determined therapy parameters following the suspension period only after receiving a confirmation in the response to the prompt.

19. The portable infusion pump of claim 13, wherein the processor is configured to determine the therapy parameters based on the information from the continuous glucose monitor.

* * * * *

UNITED STATES PATENT AND TRADEMARK OFFICE
CERTIFICATE OF CORRECTION

Page 1 of 2

PATENT NO. : 9,669,160 B2
APPLICATION NO. : 14/813699
DATED : June 6, 2017
INVENTOR(S) : Harris It is certified that error appears in the above-identified patent and that said Letters Patent is hereby corrected as shown below:

On the Title Page

Item (12) should read:
HARRIS

Item (72) Inventors:
Delete "David Berger, San Diego, CA (US)".

In the Claims

Claim 1:

Column 10, Line 15:
After "facilitate" insert -- a -- and after "delivery of" insert -- a --.

Column 10, Line 25:
After "deliver" insert -- the --.

Column 10, Line 35:
After "deliver" insert -- the --.

Column 10, Line 37:
After "stored in" insert -- the --.

Column 10, Line 38:
After "deliver" insert -- the --.

Signed and Sealed this
Tenth Day of October, 2017

Joseph Matal
*Performing the Functions and Duties of the
Under Secretary of Commerce for Intellectual Property and
Director of the United States Patent and Trademark Office*

Claim 3:

Column 10, Line 50:
After "type of" insert -- the --.

Column 10, Line 52:
After "type of" insert -- the --.

Claim 11:

Column 11, Line 56:
After "prompt" insert -- on --.

Column 11, Line 57:
After "processor that" insert -- the --.

Claim 13:

Column 12, Line 26:
Delete "determine" and insert -- determined --.